United States Patent
Gorse et al.

(10) Patent No.: US 10,301,665 B2
(45) Date of Patent: May 28, 2019

(54) DEVICE AND METHOD FOR DISPENSING A SUSPENSION OF MICROORGANISMS

(71) Applicant: BIOMÉRIEUX, Marcy l'Etoile (FR)

(72) Inventors: Florence Gorse, Charnay (FR); Bruno Colin, Marcy l'Etoile (FR)

(73) Assignee: BIOMERIEUX, Marcy l'Etoile (FR)

( * ) Notice: Subject to any disclaimer, the term of this patent is extended or adjusted under 35 U.S.C. 154(b) by 642 days.

(21) Appl. No.: 14/785,234

(22) PCT Filed: Apr. 29, 2014

(86) PCT No.: PCT/FR2014/051028
§ 371 (c)(1),
(2) Date: Oct. 16, 2015

(87) PCT Pub. No.: WO2014/177807
PCT Pub. Date: Nov. 6, 2014

(65) Prior Publication Data
US 2016/0083772 A1   Mar. 24, 2016

(30) Foreign Application Priority Data
May 3, 2013   (FR) .................. 13 54091

(51) Int. Cl.
C12M 1/00   (2006.01)
C12M 1/22   (2006.01)
C12M 1/26   (2006.01)
C12Q 1/24   (2006.01)

(52) U.S. Cl.
CPC ............. C12Q 1/24 (2013.01); C12M 23/10 (2013.01); C12M 23/38 (2013.01); C12M 33/00 (2013.01)

(58) Field of Classification Search
CPC .......... C12Q 1/24; A45D 40/00; A45D 40/26; A45D 2200/1018; A45D 2200/1036; A45D 2200/1045; A61M 35/003; C12M 21/16; C12M 23/04; C12M 23/20; C12M 23/28; C12M 23/34; C12M 23/38; C12M 41/34; C12M 23/10; C12M 33/00; Y10S 435/801; G01N 27/44704; G01N 27/44717
See application file for complete search history.

(56) References Cited

U.S. PATENT DOCUMENTS

| 2,348,448 A | 5/1944 | Brewer |
| 3,632,478 A * | 1/1972 | Fink ................. C12M 21/16 435/305.2 |
| 3,907,647 A | 9/1975 | Sanderson |
| 4,321,330 A | 3/1982 | Baker et al. |

(Continued)

FOREIGN PATENT DOCUMENTS

| EP | 1363991 B1 | 8/2007 |
| FR | 2594848 A1 | 8/1987 |

(Continued)

OTHER PUBLICATIONS

Sep. 9, 2014 International Search Rpoert issued in International Patent Application No. PCT/FR2014/051028.

*Primary Examiner* — William H. Beisner
*Assistant Examiner* — Danielle B Henkel
(74) *Attorney, Agent, or Firm* — Oliff PLC

(57) ABSTRACT

A device including an applicator capable of dispensing a suspension of microorganisms on a culture medium and to the use of the device for dispensing the suspension of microorganisms.

12 Claims, 3 Drawing Sheets

(56) References Cited

U.S. PATENT DOCUMENTS

| | | | | | |
|---|---|---|---|---|---|
| 4,565,783 | A | * | 1/1986 | Hansen | C12Q 1/04 435/30 |
| 5,134,064 | A | * | 7/1992 | Nordlund | C12M 41/36 435/288.3 |
| 5,464,521 | A | * | 11/1995 | Bellon | G01N 27/44704 204/616 |
| 6,315,482 | B1 | * | 11/2001 | Girardot | A45D 40/00 15/104.93 |
| 8,012,382 | B2 | * | 9/2011 | Kim | B01J 19/0046 216/44 |
| 2014/0016841 | A1 | * | 1/2014 | Zahniser | G06T 7/0012 382/128 |

FOREIGN PATENT DOCUMENTS

| | | |
|---|---|---|
| FR | 2639957 A1 | 6/1990 |
| FR | 2686895 A1 | 8/1993 |

* cited by examiner

DEVICE AND METHOD FOR DISPENSING A SUSPENSION OF MICROORGANISMS

The technical field of the present invention is that of in vitro diagnosis and more specifically that of microbiological diagnosis. The present invention relates in particular to a device comprising an applicator capable of dispensing a suspension of microorganisms on a culture medium. The invention also relates to a method for isolating microorganisms in a suspension of microorganisms and also to a method for counting microorganisms in a suspension of microorganisms.

The use of culture media in the microbiological field has been known for many decades to enable the growth, detection, isolation and counting of microorganisms. These culture media are commonly in the form of agar contained in a Petri dish or in a dehydrated form applied to a support, generally a film.

Dehydrated culture media on a support have been developed to replace the Petri dish. For these products, the rehydration is carried out in situ, i.e. directly in the space used for the inoculation and incubation. One of them, the Petrifilm™ system, comprising rehydratable nutrients, is very widely used. Another system developed by the company Nissui Pharmaceutical, Compact Dry, is also in the form of dehydrated media. These culture media have the advantage that they can be stored for longer than a ready-to-use agar culture medium. They can also, like Petrifilm™, take up little space and thus use a small incubation space. The surface area available for the culture is limited and the nutrients available per cell have a concentration suitable for giving colonies of smaller diameter than on conventional agar medium, it being possible for the shape of the colonies to also be modified owing to the low solidity of the gel used or the high diffusion coefficients of the bacteria.

The isolation of microorganisms on culture medium, from a sample to be analyzed or from a suspension of microorganisms, is a step that is often essential to many methods of microbiological analysis. This step is in particular used to carry out identifications, to verify the microbial purity of a sample or else to perform a bacteria count by counting the isolated colonies thus obtained. After incubation, the colonies are counted in agar medium deposited in a Petri dish or other supports. The counting can be carried out by eye or by means of an automated colony-counting device. If the amount of inoculum of the sample and the dilution ratios are known, it is possible to determine the number of microorganisms per unit volume or per unit weight of the sample, usually expressed in CFU/ml or in CFU/g (colony-forming unit), from the number of countable colonies.

Isolation techniques have the objective of attaining directly usable colonies (DUCs) at the surface of a gelled nutritive medium. They are well known to those skilled in the art, the streaking technique being the reference technique. The latter consists in depositing the inoculum by rubbing on a surface with an equal probability per unit of surface area traveled. The local density distributed decreases approximately exponentially during the travel of the instrument. Thus, several areas of plating out starting from a single inoculum are produced, with or without overlapping of the areas, in order to obtain the appropriate distribution effect and a depletion of bacteria when it comes to the subsequent plating-out segment. At the end of plating out the cells are sufficiently isolated from one another for the microbial growth in DUC form (visible colonies or microcolonies) not to be even partially superimposed. Another widespread technique, in particular for counting microorganisms, consists of isolation on a dish of agar medium by surface plating out. In this case, a mixture of cells at a low cell concentration making it possible to culture up to 300 cells is plated out at the surface of the gel of a Petri dish 9 cm in diameter, each cell developing into an isolated colony. However, when less than 5 cells are brought into contact with the nutritive gel, statistical problems distort the accuracy of the count. Furthermore, when the number counted is above 150 or 300 cells, counting errors can appear because of overlapping of the surfaces of the colonies, or possible interactions. In other cases of concentrations greater than 300 CFU/ml (colony-forming units), a bacterial culture will have a tendency to form only microcolonies because of the lack of nutritive medium. Since these microcolonies are not always visible to the naked eye, the result of this culture may be analyzed as a false negative. The plating out is usually performed with an instrument comprising, for example, a linear part which is in contact with the gel or using beads a few millimeters in diameter, which roll randomly on the surface via an uncoordinated movement. This technique is therefore suitable only for a weakly contaminated or diluted sample since a high number of cells increase the probability of confluence of the colonies resulting from the growth.

It is also possible to perform a count on a dish by incubating in the body of the agar. The starting sample is diluted so as to sufficiently reduce the microbial population and to obtain separate colonies. Small known volumes of each of the samples to be counted, and which are optionally diluted, are then mixed with a liquid gel, usually agar kept molten approximately at 45° C. The mixtures are prepared in sterile culture dishes and, after gelling and incubation, each cell is immobilized and forms a colony by cell multiplication.

In the case of dehydrated culture media on a support, colony isolation is possible only by inclusion in the gel formed during the rehydration, and therefore using a starting sample which is weakly contaminated or which has undergone a series of dilutions. The final concentration, to be deposited on the medium, must be less than 250 or 100 CFU/ml (colony-forming units), these conventional data depending on the medium used. The inoculum is poured onto the dehydrated medium and can be plated out on the surface using an applicator. This applicator makes it possible in particular to uniformly dispense the inoculum. A known applicator is the Petrifilm™ spreader from the company 3M™.

Nevertheless, when the starting sample is greatly contaminated (about 300 colony-forming units/ml), the use of these techniques requires a series of dilutions to be produced, involving a larger test sample, wasted time, and the consumption of a large number of reagents (culture medium, diluent tubes, etc.), generating a high volume of waste (autoclaving, treatment costs). Furthermore, if a large number of dilutions are produced, there is a risk of losing the target microorganism through the dilution effect, if said microorganism is present in a low amount relative to the total microflora.

U.S. Pat. No. 3,632,478 describes an applicator (20) for agar culture media which has a convex surface in order to force out any bubbles present in the suspension, and also a tine (24) intended to penetrate the culture medium in order to inoculate it deeply. This applicator is intended to remain in a position of contact with the culture medium in order to promote anaerobic growth of any microorganisms present in the suspension. However, this applicator cannot be used on dehydrated media or on agar media of any thickness. Furthermore, the convex shape of the surface of contact does not make it possible to dispense the suspension at different thicknesses. Finally, since the applicator is intended to remain in contact with the culture medium, a reading of the number of colony-forming units after incubation of the medium can be distorted by the material used. In the case where the applicator is withdrawn, some colonies could also adhere to the surface of contact and come to contaminate other surfaces.

Document EP-B1-1363991 provides a dehydrated culture medium which has a flexible film intended to uniformly dispense a suspension deposited on a dehydrated culture medium. For that, an excess thickness having a circular opening is deposited on this surface of the substrate constituting the culture medium. The suspension is deposited on the substrate, at the center of the circular opening formed by the excess thickness, and the flexible film is then folded back on the suspension in order to uniformly dispense it until it reaches the edges formed by the excess thickness. Once dispensed, the suspension therefore has a surface of uniform thickness contained by the circular opening of the excess thickness. This device does not however make it possible to dispense the suspension non-uniformly on the medium. Furthermore, a known amount of suspension must be deposited on the medium in order to limit the risks of flow.

Document FR-A1-2686895 describes a culture dish intended for culturing microorganisms, comprising a receptacle which is covered with a lid and on the bottom of which is a layer of a culture medium. The device also comprises a spreader emerging from an internal face of the lid and intended to spread an inoculum over the nutritive layer. However, the spreader or applicator does not make it possible to dispense the suspension according to different thicknesses. The use with a dehydrated culture medium is also not described.

Document FR-A1-2594848 proposes mixing a medium with a sample and solidifying it in a Petri dish comprising various compartments of defined heights. The medium thus dispensed forms layers of agar of different thicknesses. The known geometry of the dish thus makes it possible to calculate the amount of microorganisms in the principal sample, from the number of colonies counted in a compartment of defined volume. This document makes it possible to dispense with successive dilutions, but is not applicable to a dehydrated culture medium, in particular in the form of a film. Furthermore, the use of this medium requires keeping the culture medium at a temperature sufficient for mixing it with the sample and then waiting for complete solidification of the medium before incubation and then counting.

It emerges from the prior art considered that there is no isolating or counting device or method, which is simple to carry out, starting from a sample to be analyzed or from a suspension of microorganisms of unknown concentration, and which makes it possible to obtain isolated colonies or countable colonies on agar or dehydrated medium on a support.

A first objective of the present invention is to provide a device comprising an applicator capable of dispensing a suspension of microorganisms on a culture medium and the associated isolation process, more effective than the methods and devices of the prior art.

A second objective of the present invention is to provide a device comprising an applicator capable of dispensing a suspension of microorganisms on a culture medium in at least two volumes of suspension of distinct thicknesses.

A third objective of the present invention is to provide a method for isolating microorganisms from a sample having a high initial microorganism concentration.

A fourth objective of the present invention is to provide an isolation method compatible with microorganism counting.

A fifth objective of the present invention is to provide an applicator and an isolation method compatible with the use of dehydrated media on a support.

A sixth objective of the present invention is to provide a device and a corresponding method making it possible to perform a count more simply and less expensively than the current methods and devices.

These objectives, among others, are achieved by virtue of the present invention which provides a device comprising an applicator capable of dispensing a suspension of microorganisms on a culture medium which is itself deposited on a support. In its position of contact with the suspension of microorganisms, the applicator comprises at least two surfaces of contact with the suspension of microorganisms, each surface defines a plane, the at least two planes being parallel to one another and having a distance between them of a height h, the at least two parallel planes face the interface between said suspension of microorganisms and the culture medium and are also arranged parallel to said interface.

The term "applicator" is intended to mean a device capable of dispensing a suspension of microorganisms on a culture medium. This dispensing can be in the form of a layer of suspension of uniform thickness or of several thicknesses. An applicator according to the invention can be made of a large variety of materials known to those skilled in the art, such as plastics, metals or cardboards. Plastics which can be used are, for example and in a nonlimiting manner, polystyrene, polyethylene or polypropylene. The use of inexpensive plastics makes it possible to make the device single-use and disposal in order to limit the risks of contamination. The material used may be rigid or flexible in order to make it possible to dispense the suspension. The material must not be porous so as not to absorb the suspension during the dispensing. The material may thus be hydrophobic.

The dispensing can be carried out directly by contact of the applicator on the suspension of microorganisms or alternatively by placing the applicator on a protective film placed on the suspension. The applicator can be placed manually or automatically. The force required to dispense the suspension can be obtained by the weight of the applicator, the force applied by the user or any other semi-automated or automated device known to those skilled in the art.

For the purposes of the present invention, a surface of contact is a surface of the applicator capable of coming into contact with the suspension of microorganisms in order to dispense it, optionally by means of a protective film. A surface of contact is a substantially planar surface. The outline of the plane formed by the surface of contact can have a large variety of shapes. It can in particular be circular, such that at least two surface of contacts form two concentric circles. The outline of the plane formed by the surface of contact can also be any portion of a circle, for example formed by two radii starting from the center and an arc of a circle. It can also be rectangular.

The at least two surface of contacts of the applicator make it possible to dispense the suspension in at least two volumes of suspension of distinct thicknesses. The at least two surface of contacts define at least two parallel planes. The height $h$ corresponds to the smallest distance between the at least two parallel planes. The height $h$ makes it possible to define the difference in thickness obtained after dispensing the suspension between two surface of contacts. In the case of an applicator comprising only two surface of contacts, the height h makes it possible to define the difference in thickness of the two volumes of suspension dispensed by the applicator. The at least two surface of contacts can be juxtaposed or imbricated. In the case where the two surfaces are imbricated, at least one part of the first surface of contact then projects into the plane formed by the second surface of contact. Alternatively, at least one part of the first surface of contact can form a recess in the plane formed by the second surface of contact.

Alternatively, the zone located between the two surface of contacts, whether juxtaposed or imbricated, is marked by a marking means. This marking means makes it possible to mark the border between the two surface of contacts when they are placed on the culture medium. This marking means thus makes it possible to improve the counting of the colonies present on the upper part of the medium by separating the zones of different concentrations. This marking means can be produced, for example, by addition of material on the surface of contact of the applicator, which is continuous or discontinuous, making it possible to emboss the upper part of the culture medium. Alternatively, this marking means can be produced by a recess, an ink pad, a blade, an alignment of stamps or any other means, arranged in the zone located between the two surface of contacts. Alternatively, this marking means marks only the border between two surface of contacts visually and does not modify the thickness of suspension dispensed or the thickness of the culture medium.

The term "culture medium" is intended to mean a medium comprising all the constituents required for the survival and/or growth of microorganisms, which is deposited on a support. In practice, those skilled in the art will choose the culture medium according to the target microorganisms, according to criteria which are entirely known and within the scope of those skilled in the art. A culture medium can be in a dehydrated or agar form. In the case of the agar form, the culture medium is contained in a Petri dish. The support of the culture medium is in this case the flat bottom of the Petri dish. The constituents are mixed while hot and deposited in liquid form in the dish. Upon cooling, the mixture formed solidifies, and the suspension can then be deposited on the upper part of the medium.

In the case of the dehydrated or dried or lyophilized form, the constituents or a part of the constituents required for the survival and/or growth of microorganisms are applied to one or more solid supports in dry form. The suspension is then deposited on or between these solid supports. These sometimes flexible supports are kept flat during the use of the medium. Upon contact with the suspension, the constituents in dry form rehydrate and perform their function. This form of medium is particularly advantageous for preserving the constituents and also for limiting the space taken up by the medium.

The term "suspension of microorganisms" is intended to mean a liquid or viscous sample which may contain one or more microorganisms. For the purposes of the present invention, the term "microorganism" covers gram-positive or gram-negative bacteria, yeasts, molds, amoebae and more generally single-cell organisms, invisible to the naked eye, which can be manipulated and multiplied in the laboratory.

According to one preferred embodiment of the invention, the microorganism is a gram-negative or gram-positive bacterium, a yeast or a mold.

By way of example of gram-positive bacteria, mention may be made of the bacteria of the following genera: *Enterococcus, Streptococcus, Lactobacillus, Bifidobacterium, Staphylococcus, Bacillus, Listeria, Clostridium, Mycobacteria, Nocardia, Corynebacteria, Micrococcus* and *Deinococcus.*

By way of example of gram-negative bacteria, mention may be made of the bacteria of the following genera: *Escherichia, Enterobacter, Klebsiella, Salmonella, Proteus, Serratia.*

By way of example of yeasts, mention may be made of the following genera:
*Candida, Cryptococcus, Saccharomyces* and *Trichosporon.*

By way of example of molds, mention may be made of the following genera:
*Aspergillus, Penicillium, Cladosporium.*

The term "interface" is intended to mean the zone of contact between the upper part of the culture medium and the suspension of microorganisms once deposited on the culture medium. The interface generally forms a plane. In the case of an agar medium, the medium is deposited while hot on the support and solidifies upon cooling so as to form a planar upper part. Since the suspension of microorganisms is liquid, the interface between the suspension deposited and the upper part of the culture medium then forms on the same plane. In the case of a dehydrated medium, at least one part of the constituents of the culture medium is deposited on a planar support and then dehydrated, or deposited directly in dehydrated form. In these two cases, the upper part of at least one part of the constituents of the culture medium forms a plane.

The term "upper part of the culture medium" is intended to mean the part on which the suspension of microorganisms is deposited during the inoculation of the medium.

The present invention also relates to a device comprising an applicator capable of dispensing a suspension of microorganisms on a culture medium. In its position of contact with the suspension of microorganisms, the applicator comprises at least two surfaces of contact with the suspension of microorganisms, each surface defines a plane, the at least two planes being parallel to one another and having a distance between them of a height h, the at least two parallel planes face the interface between said suspension of microorganisms and the culture medium and are also arranged parallel to said interface, h being equal to $h_1-h_2$, $h_1$ being the distance between the first surface of contact and the interface, $h_2$ being the distance between the second surface of contact and interface and the $h_1/h_2$ ratio being greater than 1 and less than or equal to 100.

Preferably, the $h_1/h_2$ ratio is between 2 and 10. More preferentially, this ratio is equal to 3.

S1 corresponds to the area of the first surface of contact of the applicator and S2 corresponds to the area of the second surface of contact of the applicator.

In one particular embodiment, the $(h_1 \times S_1)/(h_2 \times S_2)$ ratio is greater than 1 and less than or equal to 1000.

In one particular embodiment, viewed perpendicular to the parallel planes formed by the surface of contacts, the areas $S_1$ and $S_2$ do not overlap, likewise the surface of contacts.

The value of the h1/h2 ratio makes it possible to define a ratio of thickness of the suspension dispensed by the surface of contacts of the zones of the applicator. The respective volumes of suspension dispensed by these two surfaces are $h_1 \times S_1$ and $h_2 \times S_2$. Thus, if the areas of the surfaces $S_1$ and $S_2$ are equal, the value of the $h_1/h_2$ ratio makes it possible to define the ratio between the two volumes of suspension dispensed by the two surface of contacts of the applicator.

More generally, it will be possible for other $h_n/h_{n+1}$ ratios to be easily defined by those skilled in the art, $h_n$ being the distance between the nth surface of contact and the interface and $S_n$ corresponds to the area of the nth surface of contact. Likewise, $h_n \times S_n$ will determine the volume dispensed by the nth surface of contact.

The advantage of the invention is therefore that it provides a device comprising an applicator capable of dispensing a volume of suspension in at least two volumes having different thicknesses and/or different surfaces, the area occupied by the surface of a volume of dispensed suspension being measured in the plane parallel to the surface of contact of the applicator. In one particular embodiment, the applicator dispenses the suspension in at least two volumes having equal surfaces and different thicknesses. In another embodiment, the applicator dispenses the suspension in at least two volumes having different surfaces and different thicknesses.

Thus, an artificial dilution is carried out starting from the initial volume of suspension, said volume being shared out over at least two volumes having known surfaces and known thicknesses. The ratio between the two volumes is then equivalent to a dilution ratio. Depending on the microorganism sought in the suspension, the height h and the areas of the at least two surfaces will be adjusted so as to allow the desired dilutions between the corresponding various volumes and surfaces. For example, the suspension can be artificially diluted one-in-three by a zone where the thickness will be three times smaller compared with another zone of which the surface is identical. The counting will therefore be easier in this zone where the suspension is artificially less concentrated, in particular in the case where the suspension is very rich in microorganisms. Dilution ratios used are, for example and in a nonlimiting manner: ⅓ or $10^{-1}$ for a suspension of microorganisms that is not very concentrated, $10^{-2}$, $10^{-3}$, $10^{-4}$, $10^{-5}$ or $10^{-6}$ for a total flora.

In one particular embodiment, the device comprises at least one means for leaving a space between the surface of contacts of the applicator and the support or the interface. As an alternative, the means for leaving a space and the applicator are interdependent. As an alternative, the means for leaving a space is independent of the applicator, such as at least one added spacer piece.

This means for leaving a space ensures a minimum distance between at least one surface of contact of the applicator and the upper part of the culture medium so as to guarantee a minimum suspension thickness regardless of the force applied by the applicator during the dispensing. As an alternative, the means for leaving a space is independent of the applicator, such as an added spacer piece which is independent of the applicator and which can be withdrawn after the dispensing of the suspension without having to withdraw the applicator.

It is not necessary for the areas of the at least two surface of contacts, S1 and S2, to cover the entire surface of the culture medium. The areas of the at least two surface of contacts can in particular cover only one part of the area of the upper part of the culture medium. To this effect, the device comprises a means for leaving a space between the surface of contacts of the applicator and the support or the interface which ensures a minimum distance between at least one surface of contact of the applicator and the upper part of the culture medium. A volume of suspension of microorganisms greater than the sum of the volumes to be dispensed, for example $(h_1 \times S_1)$ and $(h_2 \times S_2)$, can thus be deposited. In this way, even if an excess of suspension of microorganisms flows outside the areas of the surface of contacts $S_1$ and $S_2$, outside the interface, or outside the device, and thus can no longer be dispensed, the volumes dispensed by the device according to the invention remain correct. Preferentially, a gelling agent which can be included in a dehydrated culture medium, on the surface of contacts of the applicator, in the suspension of microorganisms or on the protective film placed on the suspension makes it possible to slow down the flow of the suspension and to rapidly solidify it (in less than one minute, ideally in a few seconds) when said suspension is deposited on the culture medium. In this way, the suspension can be dispensed in several volumes to be dispensed before there remains, on contact with the device according to the invention, a volume of suspension less than the sum of the volumes to be dispensed; signifying that too great a volume of suspension has flowed outside the areas of the surface of contacts $S_1$ and $S_2$, outside the interface or outside the device, it no longer being possible for this flowed volume to be dispensed.

As an alternative, the minimum distance between at least one surface of contact of the applicator and the upper part of the culture medium can be guaranteed by automated means known to those skilled in the art. As an alternative, this minimum distance is guaranteed by a manual or automated device which provides a defined force of application of the applicator on the suspension.

In one particular embodiment, the device comprises a peripheral means for confining the suspension of microorganisms. This peripheral confining means makes it possible to retain the suspension deposited on the medium so that it does not overflow the culture medium during the dispensing by the applicator. Peripheral confining means can be produced by an excess thickness of material on the applicator and/or on the culture medium and/or its support. As an alternative, these peripheral confining means can be produced by a film deposited around the culture medium, comprising at least one opening of any shape. This excess thickness can optionally form a ring, a discontinuous excess thickness or any shape capable of confining the suspension known to those skilled in the art. Advantageously, the peripheral confining means can perform the function of the means for leaving a space in order to ensure a minimum distance between at least one surface of contact of the applicator and the upper part of the culture medium. Advantageously, the excess thickness is discontinuous in order to expel, in a controlled manner, an excessively large amount of suspension deposited on the upper part of the culture medium.

Advantageously, the peripheral confining means makes it possible to confine a volume of suspension greater than the sum of the volumes dispensed by the device according to the invention, so as to confine an excess of volume of suspension having been deposited on the culture medium.

The invention also relates to a method for isolating microorganisms contained in a suspension of microorganisms, using a device according to the invention, comprising the following steps:
  a) depositing a suspension on a culture medium which is itself deposited on a support,
  b) placing an applicator on the suspension, said applicator dispensing the suspension in at least two different and determined volumes,
  c) incubating the culture medium for a time and at a predetermined temperature allowing the growth of the microorganisms.

The invention also relates to a method for isolating microorganisms contained in a suspension of microorganisms, using a device according to the invention, comprising the following steps:

a) depositing a suspension on a culture medium which is itself deposited on a support;
a') placing a protective film on the suspension;
b) placing an applicator on the film, said applicator dispensing the suspension in at least two different and determined volumes;
c) incubating the culture medium for a time and at a predetermined temperature allowing the growth of the microorganisms.

In the case of a use of the device according to the invention for dispensing a suspension of microorganisms on a culture medium, it is not necessary to use a peripheral confining means, in particular by virtue of the action of a gelling agent, it being possible for the latter to be included: in a dehydrated culture medium, on the surfaces of contact of the applicator, in the suspension of microorganisms or on the protective film placed on the suspension.

Thus, according to a particular method for using the device according to the invention, a method for isolating microorganisms contained in a suspension can comprise the following steps:
a) depositing a suspension on a culture medium which is itself deposited on a support;
a") waiting for the gelling of the suspension of microorganisms for less than one minute, so as to be able to dispense it without it flowing too much outside the interface, outside the areas of the surface of contacts $S_1$ and $S_2$ or outside the device,
b) placing an applicator on the suspension, said applicator dispensing the suspension in at least two different and determined volumes,
c) incubating the culture medium for a time and at a predetermined temperature allowing the growth of the microorganisms.

As an alternative, a step consisting in:
a') placing a protective film on the suspension, may be carried out between step a) and b) of the method previously described.

The invention also relates to a method for isolating microorganisms contained in a suspension of microorganisms, using a device according to the invention, comprising an additional step d) consisting in counting the colonies resulting from these microorganisms.

The term "protective film" is intended to mean a removable film which can be placed on the suspension of microorganisms once said suspension has been deposited on the culture medium. The protective films can be made, for example and in a nonlimiting manner, of polyethylene, polypropylene or polyvinyl chloride. The film thickness is preferentially between 30 and 120 µm. In the case where a protective film is placed between the suspension and the surface of contact of the applicator, the applicator can be reused without performing washing. As an alternative, the protective film is integrated into the applicator. As an alternative, the applicator according to the invention and the culture medium support are interdependent.

As an alternative, a gelling agent can be deposited on the internal face of the protective film. The internal face of the protective film is the face which comes into contact with the suspension of microorganisms. A gelling agent is an agent which solidifies at ambient temperature on contact with a liquid, in particular with a suspension of microorganisms. Numerous gelling agents can be used, such as and in a nonlimiting manner: guar gum, xanthan gum, locust bean gum, hydroxyethylcellulose, carboxymethylcellulose, polyacrylamide, algin, carrageenan, wax, silicone and combinations of these agents. A gelling agent makes it possible to solidify a suspension of microorganisms deposited on a culture medium in less than one minute, generally in a few seconds, so that the suspension can be dispensed by the device according to the invention without too large a volume flowing outside the interface, the areas of the surface of contacts or the growth zone of the culture medium, ideally without the suspension flowing or leaking outside the interface, the areas of the surface of contacts or the growth zone of the culture medium. A flowed volume which is too large signifies the volume of suspension that can still be dispensed by the device according to the invention after said suspension has been deposited and has flowed is less than the sum of the volumes to be dispensed, defined by the device according to the invention.

As an alternative, a gelling agent can be added to the suspension. This addition makes it possible in particular to improve the use of a device according to the present invention with an agar medium. In this embodiment, the suspension containing the gelling agent is dispensed on an agar medium with the applicator according to the invention. After solidification of the gelling agent, and therefore of the suspension, the applicator can thus be withdrawn, in particular in order to facilitate the reading of the growth after incubation.

As an alternative, the invention also relates to a method for counting microorganisms contained in a suspension of microorganisms, using a device according to the invention, comprising the following steps:
a) depositing a suspension on a culture medium which is itself deposited on a support;
b) placing an applicator on the suspension, said applicator dispensing the suspension in at least two different volumes,
c) incubating the culture medium for a time and at a predetermined temperature allowing the growth of the microorganisms;
d) counting the colonies resulting from these microorganisms.

As an alternative, the invention also relates to a method for counting microorganisms contained in a suspension of microorganisms, using a device according to the invention, comprising the following steps:
a) depositing a suspension on a culture medium which is itself deposited on a support;
a') placing a protective film on the suspension,
b) placing an applicator on the film, said applicator distributing the suspension in at least two different and determined volumes,
c) incubating the culture medium for a time and at a predetermined temperature allowing the growth of the microorganisms;
d) counting the colonies resulting from these microorganisms.

As an alternative, the culture medium is dehydrated, dried or lyophilized.

As an alternative, the method for isolating or counting according to the invention comprises a step, preliminary to step b), consisting in placing an added spacer piece on the culture medium.

As an alternative, the method for isolating or counting according to the invention comprises a step, preliminary to step a), consisting in placing a peripheral confining means on the culture medium.

The invention also relates to the use of a device according to the invention for carrying out a method for isolating or counting microorganisms.

The invention will be understood more clearly on reading the following examples, which are in no way limiting, with reference to the drawings. In the interests of simplification, the parts or elements of an embodiment which occur identically or similarly in another embodiment will be identified by the same numerical references and will not be once again described.

FIGS. 1A and 1B are diagrammatic representations of the applicator included in the device according to the invention.

The applicator (10) comprises at least two surfaces of contact (11, 12) with the suspension of microorganisms on at least two parallel planes which have a distance between them of a height h.

The shape of the applicator (10) as represented in the figures is not limiting, it being possible for said applicator to be cylindrical, parallelepipedal, frustoconical or any shape, known to those skilled in the art, capable of having at least two surfaces of contact with the suspension of microorganisms on at least two parallel planes which have a distance between them of height h. The main axis of the shape of the applicator is generally perpendicular to the plane formed by a surface of contact. The device can alternatively have a grasping means located on the surface opposite the surfaces of contact. This grasping means facilitates the manipulation of the applicator by an operator, in particular during the dispensing of the suspension.

Figure 1A:
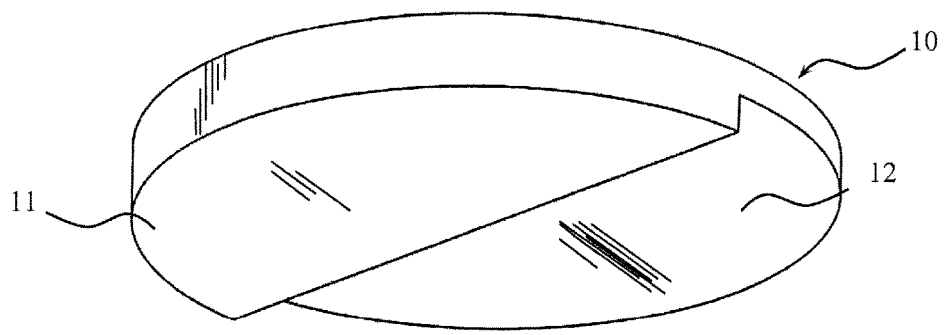
FIG. 1A represents one particular embodiment of the invention comprising a first surface of contact (11) and also a second surface of contact (12).
Figure 1B:
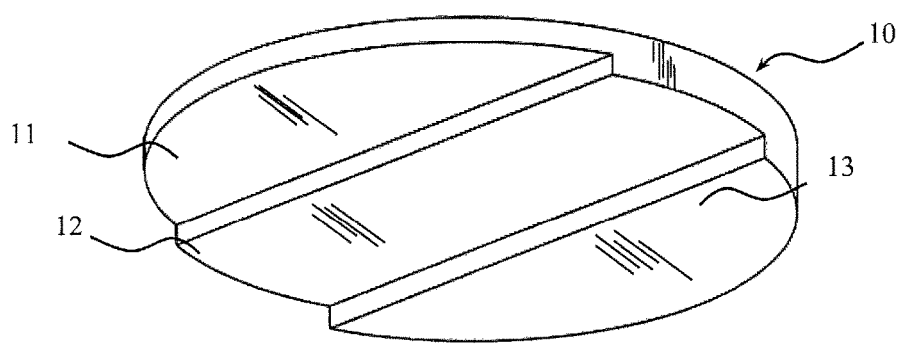
FIG. 1B represents an alternative embodiment of the invention comprising a first surface of contact (11), a second surface of contact (12) and also a third surface of contact (13).
Figure 2A:
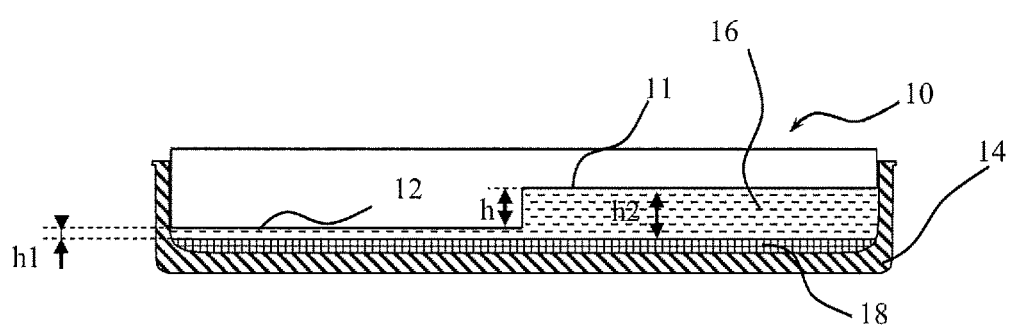
Figure 2B:
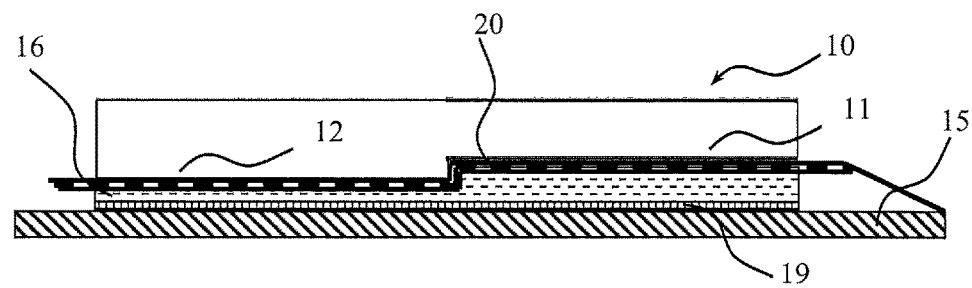

FIGS. 2A and 2B are diagrammatic representations of the device according to the invention.

FIG. 2A represents the applicator (10) having dispensed a suspension (16) on a culture medium (18) placed in a Petri dish (14). The two surfaces of contact (11, 12) with the suspension of microorganisms (16) face the interface between the suspension of microorganisms and the culture medium and dispense the suspension over two thicknesses. The two surfaces of contact (11, 12) with the suspension of microorganisms (16) are also placed parallel to the interface between the suspension of microorganisms and the culture medium. The two surfaces of contact (11, 12), viewed perpendicular to the parallel planes formed by the surfaces of contact (11, 12) and their respective areas S1 and S2, do not overlap and have an outline formed from a diameter of a circle and the corresponding arc. The height h and also the distances h1 and h2 are also represented. In this embodiment, the outline of the surfaces of contact (11, 12) cooperates with the wall of the Petri dish in order to dispense the suspension over two single thicknesses and to prevent any leaking of the suspension outside the areas of the surfaces of contact, $S_1$ and $S_2$.

FIG. 2B represents the applicator (10) having dispensed a suspension (16) on a dehydrated culture medium (19) placed on a support (15) in the form of a film. A protective film (20) is placed on the suspension of microorganisms (16). The two surfaces of contact (11, 12) with the suspension of microorganisms dispense the suspension over two thicknesses via the protective film (20). The two surfaces of contact (11, 12) face the interface between the suspension of microorganisms and the culture medium and are also arranged parallel to said interface.

Figure 3:
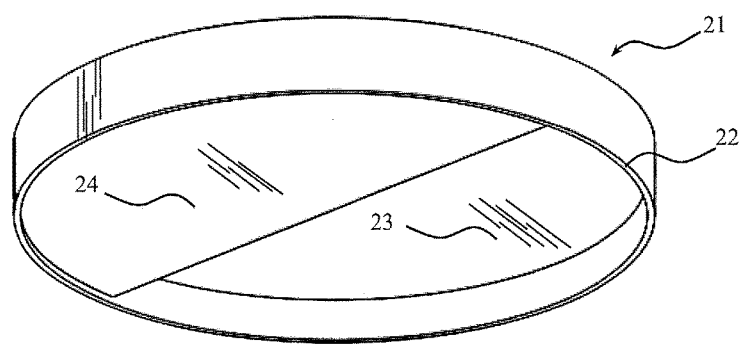

FIG. 3 represents another embodiment of the applicator according to the invention. In this embodiment, the applicator (21) comprises a means for leaving a space in the form of a ring (22) capable of maintaining the surfaces of contact (23, 24) at a defined distance from the upper part of the culture medium during the dispensing.

Figure 4:
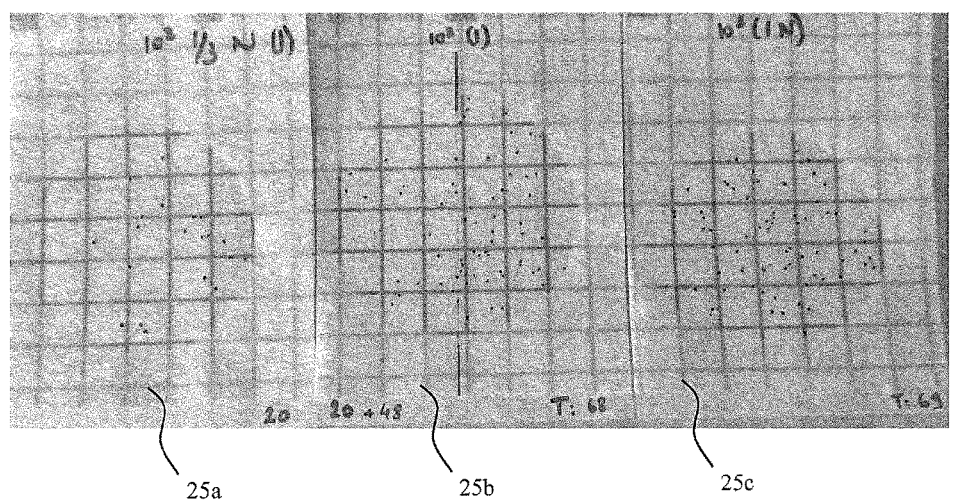

FIG. 4 represents three photographs of Petrifilm® AC 3M culture medium ref. 6400 used with a prior art applicator (25a, 25c) in comparison with an applicator according to the invention (25b).

EXAMPLES

Method

Starting from a preculture on a TSA dish produced by bioMérieux ref 43011 of the *Escherichia coli* ATCC 25922 strain, two bacterial suspensions (denoted suspension 1 and suspension 2) calibrated at ~0.4 MacFarland are prepared so as to have ~$10^8$ CFU/ml.

Each suspension is then diluted to obtain $10^2$ CFU/ml.

Starting from suspension 2 at $10^2$ CFU/ml, a further dilution is carried out in order to obtain ~60 CFU/ml. Furthermore, each suspension at $10^2$ CFU/ml is diluted to ⅓.

Petrifilm® AC 3M ref 6400 films are then inoculated with 1 ml of the various test suspensions. These Petrifilms have a culture medium 6 cm in diameter. These culture media in dehydrated form are used for counting the total flora. The protective film of the Petrifilm® is then folded back on the sample.

Example 1: Counting Bacterial Suspension 1 Using a Device According to the Invention A series of two first films is inoculated with suspension 1 diluted to ⅓. A second and a third series of two films are inoculated with suspension 1 without dilution.

A plastic applicator of the prior art, called 3M applicator, having a planar surface of contact, is placed at the center of the Petrifilm® films of the first and third series. A plastic applicator according to the invention, called bioMérieux LTN applicator, is used. This applicator is circular and has two surfaces of contact. The smallest distance between the two surfaces of contact is 0.25 mm. The applicator is placed at the center of the Petrifilm® films of the second series on the protective film. A 0.25 mm spacer piece is also placed at the periphery of the surfaces of contact. The respective thicknesses of the volumes of suspensions dispensed by the applicator are then 0.25 mm (D½) and 0.50 mm (D1), D1 corresponding to the thickness of the spacer piece, added to the smallest distance between the two surfaces of contact. This applicator makes it possible to dispense a sample in two volumes of different thicknesses and therefore in two zones of different thicknesses which simulate two dilutions of the sample to ⅔ and ⅓, each of the surfaces of contact corresponding to a zone.

The suspensions are uniformly dispensed by exerting a slight pressure at the center of the plastic applicators. The inoculum is then dispensed over the whole of the growth zone before the gel forms.

The three Petrifilm® films are then incubated at 35° C.

The *E. coil* strain chosen exhibits good growth, the colonies can be counted starting from 24 h at 35° C., and an extended incubation is not therefore envisioned.

The inoculations carried out with the 3M applicator show, after incubation, a uniform distribution of the colonies on the counting film as described in the 3M documentation.

FIG. 4 shows three photos of the three inoculated films, taken after 24 h of incubation.

A count is performed.

The first film (22a), inoculated with suspension 1 diluted to ⅓ and applied with the 3M applicator, comprises 20 counted colonies.

The second film (22b), inoculated with suspension 1 without dilution and applied with the bioMérieux LTN applicator, comprises 20 colonies in a first zone and 48 colonies in a second zone, i.e. a total of 68 colonies.

The third film (22c), inoculated with suspension 1 without dilution and applied with the 3M applicator, comprises 69 counted colonies.

The inoculations carried out with the bMx LTN applicator show, after incubation, a variable presence of the colonies on the film, according to the zone under consideration, as expected.

The LTN applicator makes it possible to count the Petrifilm over its entire surface or by zone.

For each suspension, the results obtained per ml, i.e. using the entire surface of the Petrifilms, are equivalent regardless of the applicator used.

The count using the LTN applicator, in a zone that is not very concentrated, corresponds to a third of the overall concentration or of the concentration per ml. The results correspond, on the one hand, to a third of the total count of the Petrifilms on nondiluted suspensions and, on the other hand, to the total count of the suspensions diluted to ⅓, before inoculation.

The results of the count are:

|  | First series, solution 1 at $10^2$ CFU/ml diluted to ⅓ - 3M applicator | Second series, solution 1 at $10^2$ CFU/ml - bioMérieux LTN applicator | First series, solution 1 at $10^2$ CFU/ml - 3M applicator |
|---|---|---|---|
| Number of colonies of the first film | 20 | 20 + 48 = 68 | 69 |

In one alternative embodiment, a 3 mm spacer piece is placed at the periphery of the surfaces of contact and the respective thicknesses of the volumes of suspensions dispensed by the applicator are then 3 mm (D2/2) and 6 mm (D2); the volume of suspension used to inoculate the medium is then adjusted. In another alternative embodiment, a 3 mm spacer piece is placed at the periphery of the surfaces of contact and the respective thicknesses of the volumes of suspensions dispensed by the applicator are then 3 mm (D3/3) and 9 mm (D3); the volume of suspension used to inoculate the medium is then adjusted.

Example 2: Counting Bacterial Suspension 2 Using a Device According to the Invention A series of two first films is inoculated with suspension 2 diluted to ⅓. A second and a third series of two films are inoculated with suspension 2 without dilution.

A plastic applicator from the prior art, called 3M applicator, which has a planar surface, is placed at the center of the Petrifilm® films of the first and third series. A plastic applicator according to the invention and a spacer piece according to example 1 are placed at the center of the Petrifilm® films of the second series. A 0.25 mm spacer piece is placed at the periphery of the surfaces of contact. The respective thicknesses of the volumes of suspensions dispensed by the applicator are then 0.25 mm (D½) and 0.50 mm (D1).

The suspensions are uniformly dispensed by exerting a slight pressure at the center of the plastic applicators. The inoculum is then dispensed over the whole of the growth zone before the gel forms.

The three Petrifilm® films are then incubated at 35° C.

The E. coli strain chosen exhibits good growth, the colonies can be counted starting from 24 h at 35° C., and extended incubation is not therefore envisioned.

The inoculations carried out with the 3M applicator show, after incubation, a uniform distribution of the colonies on the counting film as described in the 3M documentation.

The inoculations carried out with the bioMérieux LTN applicator show, after incubation, a variable presence of the colonies on the film, according to the zone under consideration, as expected. In the second series, the first and second films exhibit two different concentration zones. 64 colonies are counted in the first zone of the first medium, 71 in the first zone of the second medium. 35 colonies are counted in the second zone of the first medium, 34 in the second zone of the second medium.

The results of the count are:

|  | First series, solution 2 at $10^2$ CFU/ml - 3M applicator | Second series, solution 2 at $10^2$ CFU/ml - bioMérieux LTN applicator | First series, solution 2 at $10^2$ CFU/ml diluted to ⅓ - 3M applicator |
|---|---|---|---|
| Number of colonies of the first film | 111 | 64 + 35 = 99 | 35 |
| Number of colonies of the second film | 101 | 71 + 34 = 105 | 35 |

Example 3: Counting Bacterial Suspension 2 at 60 CFU/ml Using the Device According to the Invention A first series of two films is inoculated with suspension 2 diluted to 60 CFU/ml. A second series of two films is also inoculated with suspension 2 diluted to 60 CFU/ml.

A 3M applicator is placed at the center of the Petrifilm® films of the first series. A bioMérieux LTN applicator and a spacer piece according to example 1 are placed at the center of the Petrifilm® films of the second series. The suspensions are uniformly dispensed by exerting a slight pressure at the center of the plastic applicators. The inoculum is then dispensed over the whole of the growth zone before the gel forms.

The four Petrifilm® films are then incubated at 35° C.

The E. coli strain chosen exhibits good growth, the colonies can be counted starting from 24 h at 35° C., and extended incubation is not therefore envisioned.

The inoculations carried out with the 3M applicator show, after incubation, a uniform distribution of the colonies on the counting film as described in the 3M documentation.

A count is performed.

The first series of films, inoculated with suspension 2 diluted to 60 CFU/ml, applied with the 3M applicator, comprises 67 and 48 counted colonies.

The second series of films, inoculated with suspension 2 diluted to 60 CFU/ml, applied with the bioMérieux LTN applicator, comprises 36 colonies in a first zone and 18 colonies in a second zone, i.e. a total of 54 colonies for the first film, and 47 colonies for the second film.

The results of the count are:

|  | First series, solution 2 diluted to 60 CFU/ml - 3M applicator | Second series, solution 2 diluted to 60 CFU/ml - bioMérieux LTN applicator |
|---|---|---|
| Number of colonies of the first film | 67 | 36 + 18 = 54 |
| Number of colonies of the second film | 48 | 32 + 15 = 47 |

These three examples demonstrate the reproducibility of a bacterial count, according to a level of dilution defined by the shape of the surfaces of contact of an applicator placed on a culture medium not selective for microorganisms.

The bioMérieux LTN applicator produced coherent and repeatable results, while at the same time reducing the number of dilutions and of films to be inoculated.

The invention claimed is:

1. A method for isolating microorganisms contained in a suspension of microorganisms, comprising the following steps:
   a) depositing a suspension of microorganisms on a culture medium that is deposited on a support,
   b) placing an applicator on the suspension of microorganisms without penetrating the culture medium to dispense the suspension of microorganisms in at least two different volumes of distinct thicknesses under the applicator, and
   c) incubating the culture medium for a time and at a predetermined temperature so as to allow growth of the microorganisms, wherein:
       the applicator comprises at least first and second surfaces of contact that are positioned in contact with the suspension of microorganisms;
       each surface defines a plane such that at least two planes are parallel to one another and a distance between the two parallel planes is a height h; and
       each plane faces and is parallel to an interface between the suspension of microorganisms and the culture medium.

2. The method as claimed in claim 1, further comprising an intermediate step, between steps a) and b), that comprises placing a protective film on the suspension of microorganisms, wherein step b) comprises placing the applicator on the protective film so as to indirectly place the applicator on the suspension of microorganisms.

3. The method as claimed in claim 1, further comprising an additional step d) that comprises counting colonies resulting from the growth of the microorganisms.

4. The method as claimed in claim 1, wherein the culture medium is dehydrated prior to step a).

5. The method as claimed in claim 1, further comprising a step, prior to step b), that comprises placing a spacer piece on the culture medium.

6. The method as claimed in claim 1, further comprising a step, prior to step a), that comprises placing a peripheral confining means on the culture medium.

7. The method as claimed in claim 1, wherein h is equal to $h_1-h_2$, $h_1$ being the distance between the first surface of contact and the interface, $h_2$ being the distance between the second surface of contact and the interface, and the $h_1/h_2$ ratio is greater than 1 and less than or equal to 100.

8. The method as claimed in claim 7, wherein $S_1$ corresponds to the area of the first surface of contact of the applicator and $S_2$ corresponds to the area of the second surface of contact of the applicator, and the $(h_1 \times S_1)/(h_2 \times S_2)$ ratio is greater than 1 and less than or equal to 1000.

9. The method as claimed in claim 8, wherein when viewed perpendicular to the parallel planes, $S_1$ and $S_2$ do not overlap and the surfaces of contact do not overlap.

10. The method as claimed in claim 7, wherein $h_1/h_2$ is equal to 3.

11. The method as claimed in claim 1, wherein the culture medium is incubated so as to allow colonies of the microorganisms to form on a top surface of the culture medium.

12. The method as claimed in claim 1, wherein the applicator is placed over an entire top surface of the culture medium.

* * * * *